(12) United States Patent
Mosnier et al.

(10) Patent No.: US 7,294,140 B2
(45) Date of Patent: Nov. 13, 2007

(54) DEVICE FOR HOLDING TROCAR SLEEVES

(75) Inventors: Henry Mosnier, Rueil Malmaison (FR); Christophe Lafond, Compiègne (FR)

(73) Assignee: Karl Storz GmbH & Co. KG (DE)

( * ) Notice: Subject to any disclaimer, the term of this patent is extended or adjusted under 35 U.S.C. 154(b) by 553 days.

(21) Appl. No.: 10/430,072

(22) Filed: May 6, 2003

(65) Prior Publication Data
US 2003/0225422 A1  Dec. 4, 2003

(30) Foreign Application Priority Data
May 6, 2002  (EP) ................................. 02010059

(51) Int. Cl.
*A61B 17/00* (2006.01)
*A61C 3/14* (2006.01)
(52) U.S. Cl. ...................... 606/206; 606/205; 606/207; 606/208; 606/120; 433/159; 81/416
(58) Field of Classification Search ........ 606/205–208, 606/120; 433/159; 604/174; 81/300, 321, 81/394, 416; 72/409.01, 0.02; 294/3; 29/268
See application file for complete search history.

(56) References Cited

U.S. PATENT DOCUMENTS

| | | | | |
|---|---|---|---|---|
| 819,304 A | * | 5/1906 | McKinney et al. | 254/251 |
| 3,029,514 A | * | 4/1962 | Reiter | 433/154 |
| 3,172,133 A | * | 3/1965 | Rizzo | 7/132 |
| 4,633,558 A | * | 1/1987 | Spaulding | 29/229 |
| 5,269,804 A | * | 12/1993 | Bales et al. | 606/205 |
| 5,616,143 A | * | 4/1997 | Schlapfer et al. | 606/61 |
| 5,626,597 A | | 5/1997 | Urban et al. | 606/170 |
| 6,039,725 A | | 3/2000 | Moenning et al. | 606/1 |
| 6,656,205 B1 | * | 12/2003 | Manhes | 606/205 |

FOREIGN PATENT DOCUMENTS

DE  41 15 548 A1  11/1991

* cited by examiner

*Primary Examiner*—(Jackie) Tan-Uyen Ho
*Assistant Examiner*—Amanda Adams
(74) *Attorney, Agent, or Firm*—St. Onge Steward Johnston & Reens LLC

(57) ABSTRACT

A device for holding a trocar sleeve in its position of engagement in the body of a patient has clamping jaws which in the closed position define an opening and which can be placed about the outside of the trocar sleeve, and at least one hole via which the device can be fixed on the patient. The device is designed as a forceps with two forceps arms which at their area of intersection are connected to one another via a hinge and which at their distal ends in each case have at least one clamping jaw, a spring being arranged between the forceps arms, which spring is supported on the forceps arms via its long ends and forces the clamping jaws into the closed position.

19 Claims, 3 Drawing Sheets

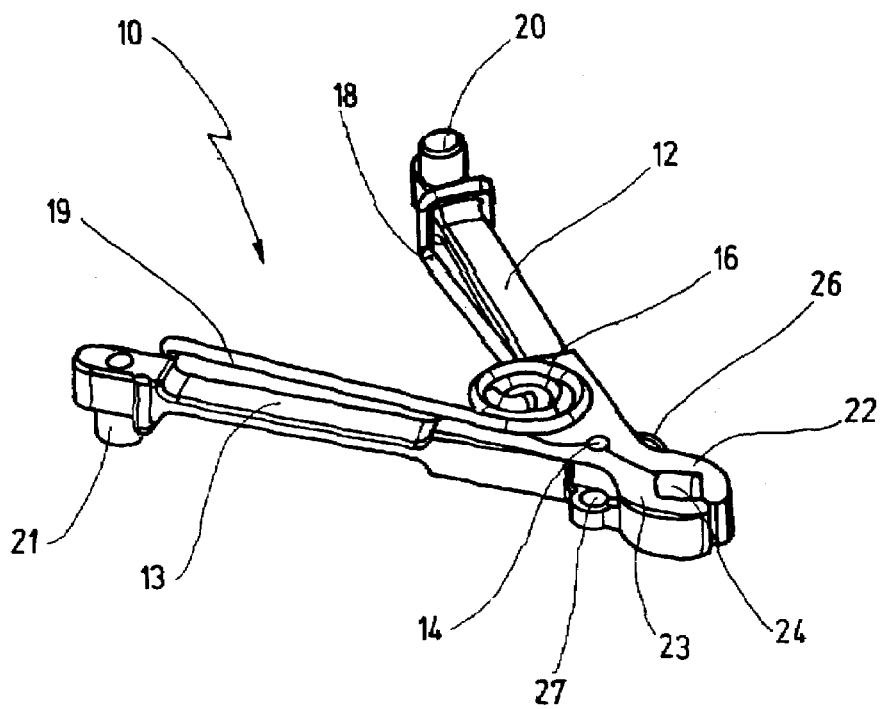
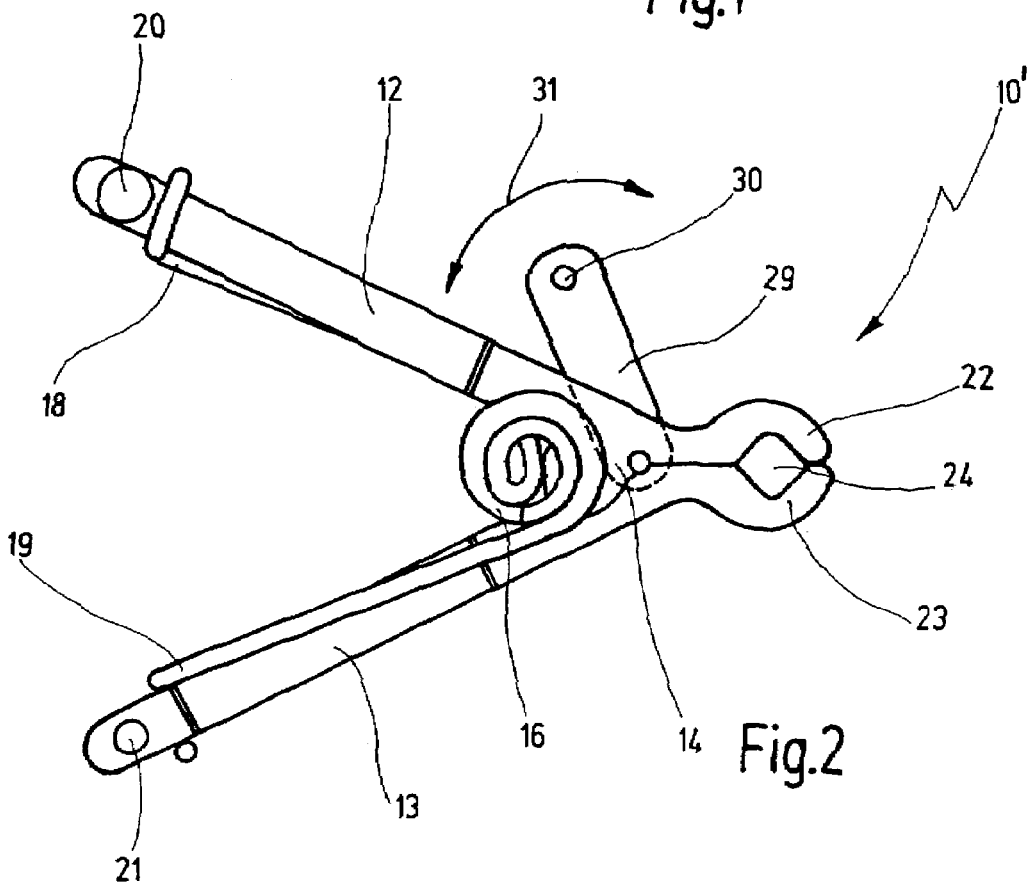

DEVICE FOR HOLDING TROCAR SLEEVES

This application claims priority of pending European Patent Application No. 02 010 059.9 filed May 6, 2002.

BACKGROUND OF THE INVENTION

The present invention relates to a device for holding a trocar sleeve in its position of engagement in the body of a patient, with clamping jaws which in the closed position define an opening and which can be placed about the outside of a trocar sleeve, and with at least one hole via which the forceps can be fixed on the patient.

A device of this kind is known in the form of a fixing disk sold by the Applicant under number 27105 AG.

Holding devices of this kind are used to hold trocar sleeves or similar surgical instruments in a defined position.

However, a disadvantage of the known trocar-fixing disks is that their relatively large surface area and rigidity means that they cannot be applied on uneven body surfaces in particular. This is the case, for example, in operations in the throat or neck area where the body surface of the patient offers no possibility of securing a holding device in the form of a flat plate or disk.

Another disadvantage is that a relatively large area of the patient's body is covered by the disks, as a result of which this area cannot be seen by the attending physician, nor is it accessible to other instruments. In minimally invasive interventions, several trocars are usually fitted, for example one for observing the operating site with an endoscope, and a second one for the actual operating instrument.

As a result of the relatively large surface area covered by the disk, it is also not possible, near the inserted trocar sleeve, to introduce further operating instruments into the patient's body or fix them on the body.

Automated, robot-like positioning systems for trocars and instruments are also known. Such devices have multi-component articulated arms whose individual elements can be oriented in different axes independently of one another. Thus, the instrument to be fixed can be held in any desired position.

However, such devices are highly complicated, very difficult to produce and to handle, and in addition are extremely expensive. Moreover, holding systems of this kind require a large amount of space in the operating room and additionally impede the operating surgeon when they are arranged next to the operating table and over the patient. A further disadvantage of these systems is that the trocars can only be fixed relative to an operating apparatus.

Therefore, it is an object of the present invention is to provide a device for holding a trocar sleeve, which device is easy to use, takes up little space, and can also be fixed securely on uneven surfaces.

SUMMARY OF THE INVENTION

This object is achieved by the fact that the device is designed as a forceps with two forceps arms which are connected to one another via a hinge and which at their distal ends in each case have at least one clamping jaw, a spring being arranged between the forceps arms, which spring is supported on the forceps arms via its elongate ends and forces the clamping jaws into the closed position.

The device according to the invention affords the advantage that, because of its design as forceps, it can also be used on uneven body surfaces for holding a trocar sleeve, since the branches can be swiveled into a favorable position in each case and stand away from the trocar which is to be held.

The device according to the invention also affords the advantage that further operating instruments and/or trocars can be introduced into a patient's body in immediate proximity to a trocar sleeve fixed by such a device and can likewise be fixed there. This is necessary, for example, when a fixed trocar sleeve is used for the introduction of surgical instruments with which internal tissues or organs are to be treated, while at the same time these steps are to be monitored via an endoscope in a trocar sleeve fitted immediately adjacent. The body surfaces surrounding the fixed trocar sleeves still remain visible to the treating physician.

The clamping jaws of the device according to the invention, which are held in the closed position by a spring, can be opened by pressing the forceps arms together counter to the pressure of the spring. The opened clamping jaws can then be placed about a trocar sleeve. By releasing the forceps arms, the clamping jaws are pressed onto the outside of the trocar sleeve on account of the force of the spring, by which means the forceps are secured immovably on the trocar sleeve. This ensures that the trocar sleeve thus fixed in the axial direction cannot penetrate any farther inward. Possible internal injuries which can be occasioned by an unfixed trocar sleeve penetrating too deep are thus avoided. If the forceps arms are impeding a maneuver, an operating surgeon can simply take hold of the forceps, slightly release the bearing pressure, and swivel the device about the trocar axis.

In a preferred embodiment, the at least one opening is present in a pivotable bracket which is arranged on the device according to the invention.

The bracket can be arranged pivotably on the forceps arms or via the hinge connecting the forceps arms. The bracket is, for example, in the form of an elongate, flat tab which comprises the at least one opening.

The bracket can have just one opening or several openings via which the device can be fixed on the patient's body. Moreover, several brackets with at least one opening can be provided.

It is advantageous if the bracket is designed in the form of an elongate, flat tab and is arranged via the hinge. In this way, the forceps arms can also be pressed together when the forceps is fixed on the patient's body by suturing via the opening present in the bracket.

This measure also has the advantage that the device in the fixed state can be swiveled as a unit about the hinge as its pivot point.

The pivotable bracket can be designed so that it can be fixed in a defined pivot position relative to one of the clamping jaws or relative to a midplane between the clamping jaws.

In a preferred embodiment, the device has at least two openings on the sides at the distal end area of the forceps arms near the clamping jaws.

The device whose clamping jaws are placed about the trocar sleeve can be fixed on the patient's body via these openings, for example by suturing, and then additionally prevent undesired withdrawal of the trocar sleeve. Once the physician has decided on the position of the trocar sleeve relative to the patient, he can place the clamping jaws of the device about the trocar sleeve, securely clamp the latter and then suture the device onto the patient via the openings, as a result of which the trocar sleeve is also fixed axially in both directions in its position relative to the patient's body. The shape of the openings can vary and can have a round, square or oblong circumference.

The device can also be secured to the patient's body by adhesive.

The device can also have more than two openings, via which the device can be fixed to the patient's body in an even more stable manner.

The device according to the invention thus affords in particular the advantage that, in operations performed especially in the throat/neck area, the trocar sleeves can be held in a stable manner and fixed so as to avoid undesired relative movements of the instruments to be manipulated in relation to the patient and thus avoid associated risks of injury to the spinal cord and/or the spinal column.

Compared to fixing aids with screw elements or tensioning elements, the device according to the invention further affords the advantage that it allows the trocar sleeve to be fixed in the above-described manner with a single and simple maneuver. The device can be activated with one hand and can be opened and closed by simple application of pressure and release of pressure. In this way, operating steps can be carried out more quickly and more easily.

The length of the forceps arms can be adapted to the particular area of use and can in particular be short in operations carried out on the neck. This ensures that the forceps arms do not impede the treating physician in subsequent further surgical interventions.

In a further preferred embodiment, the elongate ends of the spring are supported via two pins which are removable from the forceps arms.

This measure ensures that the spring lies secured and stable between the forceps arms. For cleaning, the pins are removed and the spring detached from the forceps body.

In a further embodiment of the invention, the pins are arranged at the proximal part of the forceps arms.

This measure has the advantage that the arms of the spring extend along the forceps arms and do not constitute components which take up a lot of space and impede vision.

The pins can be entirely solid, or, in order to minimize weight, they can be hollow, and their design can for example be cylindrical, conical, or square, symmetrical or asymmetrical.

In a further embodiment, the forceps arms have two pairs of clamping jaws, said pairs of clamping jaws defining, in the closed position, openings situated at a distance from one another.

This measure has the advantage that two trocars can be held simultaneously with the device. In this way, only one device needs to be used, as a result of which fewer instruments overall have to be manipulated in an intervention.

In a development of the embodiment, the distance between the openings formed by the clamping jaws is adjustable.

This measure has the advantage that, when using two trocars for example, these can be introduced into a patient's body at a flexible distance from one another. The clamping jaws can in this case be shifted on the distal ends of the forceps arms, which are designed as slides for this purpose, and can be adapted to the spacing between the trocars. The clamping jaws can be fixed on the forceps arms via adjusting screws which are for example to be introduced laterally through the clamping jaws.

With the device, both trocars can then be fixed via the openings formed by the clamping jaws. The device is then secured on the patient's body, for example by suturing.

In a further preferred embodiment, the clamping jaws have a surface which is arc-shaped in cross section perpendicular to the trocar axis. In this connection, it is preferable if the surface is made concave toward the opening formed by the clamping jaws.

This ensures that the clamping surface of the clamping jaws is adapted to the trocar sleeves. Trocar sleeves in most cases have a cylindrical shape, or they are designed cylindrically at the position where the forceps are to be applied. By means of the arc-shaped configuration of the clamping jaws, the pressure exerted on the outer wall of the trocar sleeve by the spring of the forceps is distributed uniformly on the circumference of the cylindrical surface of the trocar sleeve.

However, the shape of the opening formed by the clamping jaws can as a whole also be made square, for example, and symmetrical or asymmetrical, in particular adapted to the outer surface shape of the trocar sleeve. On their side facing the opening, the clamping jaws can also have a ridged surface, for example, by means of which the trocar sleeve can be still better gripped.

In a preferred embodiment, the opening of the device measures ca. 3 to 5 mm in size. In this way, trocar sleeves of fairly small diameter can be held securely.

In another embodiment, the clamping jaws in the closed position form an opening of 5 to 10 mm. In this way, trocar sleeves of fairly large diameter can also be arranged in the opening of the device. This is desirable, for example, for devices which are used in laparoscopy interventions.

It is preferred that the device according to the invention is made of a material selected from metal, in particular light metal, and plastic.

It is further preferred that the metal is aluminum.

These measures have the advantage that the device is very light. The inherent weight of the forceps does not substantially affect the trocar sleeve gripped by it, so that there is no risk of the trocar sleeve being withdrawn from its position in the patient's body by the weight of the forceps. By means of the light weight, the device is also particularly easy to use with just one hand.

In particular because of its small design and because of its light weight, the device is also comparatively inexpensive to produce.

It will be appreciated that the features mentioned above and the features still to be explained below can be used not just in the particular combination indicated, but also in other combinations, or in isolation, without thereby departing from the scope of the present invention.

BRIEF DESCRIPTION OF THE DRAWINGS

Illustrative embodiments of the invention are shown in the drawings and are explained in detail in the description below. In the drawings:

FIG. 1 shows a diagrammatic, perspective view of an embodiment of the device according to the invention;

FIG. 2 shows a diagrammatic view of another embodiment of the device according to the invention, in a plan view;

DETAILED DESCRIPTION OF PREFERRED EMBODIMENTS

Figure 3:
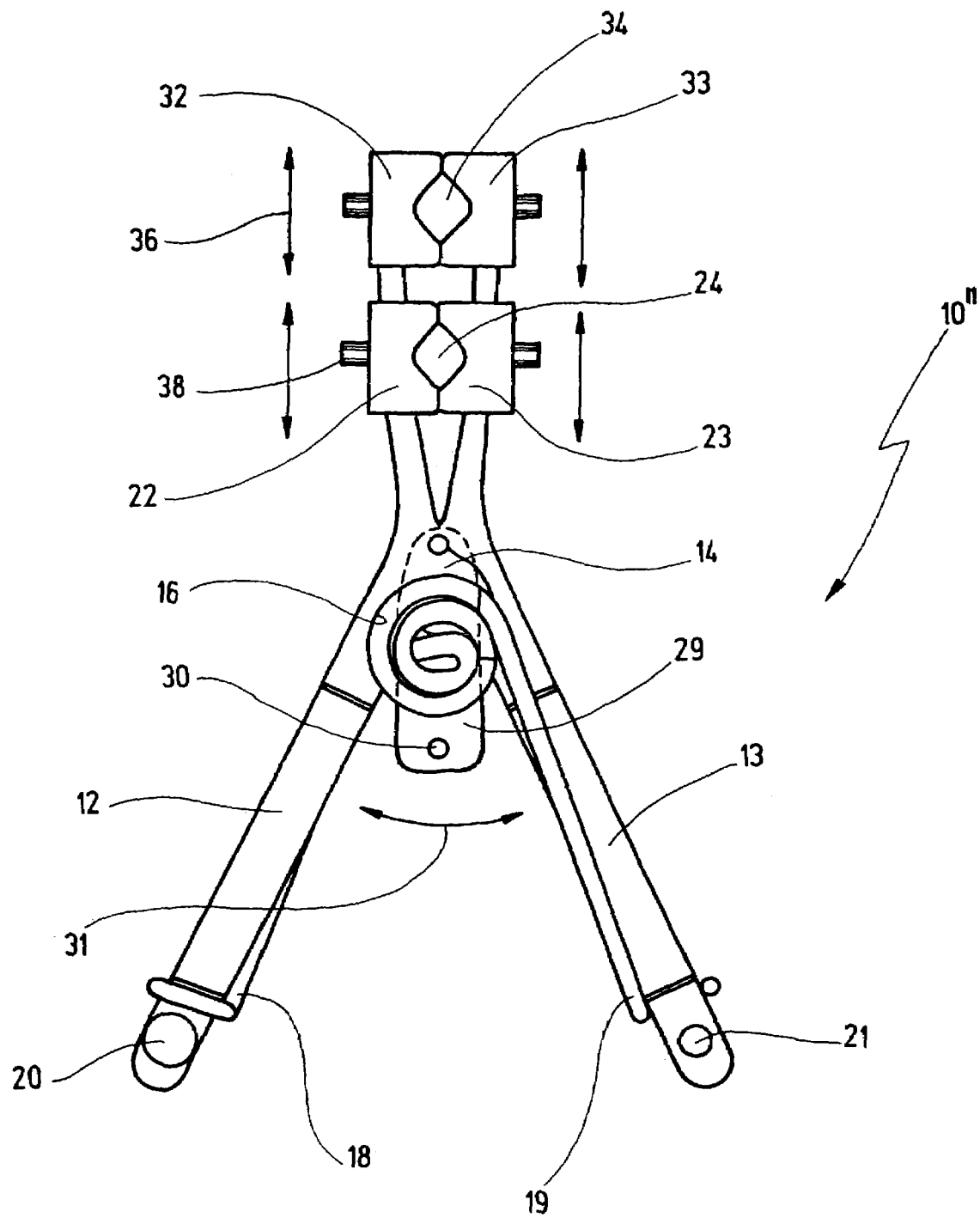
FIG. 3 shows a diagrammatic view of a further embodiment of the device according to the invention, in a plan view.

In the devices shown in the figures, reference number 10 designates the forceps as a whole, while reference numbers 12 and 13 designate the two forceps arms. The two forceps arms 12 and 13 are connected to one another via a hinge 14 at the area of intersection. A central spiral spring 16 holds the forceps arms 12 and 13 away from one another in the closed end position.

The elongate ends 18 and 19 of the spiral spring 16 are each supported on the forceps arms 12 and 13 via respective pins 20 and 21, which pins 20 and 21 are each mounted on the forceps arms 12 and 13. As is shown in FIG. 2, the section 19 of the spring 16 is placed above the forceps arm 13 and along the latter, is angled off at the proximal end of the forceps and guided round the forceps arm 13 and supported on the pin 21 arranged there. On account of the configuration of the spring 16, the section 18 is placed under the forceps arm 12 and along the latter, is angled off at the proximal end and guided round the forceps arm 12 and supported on the pin 20 arranged there.

Figure 4:
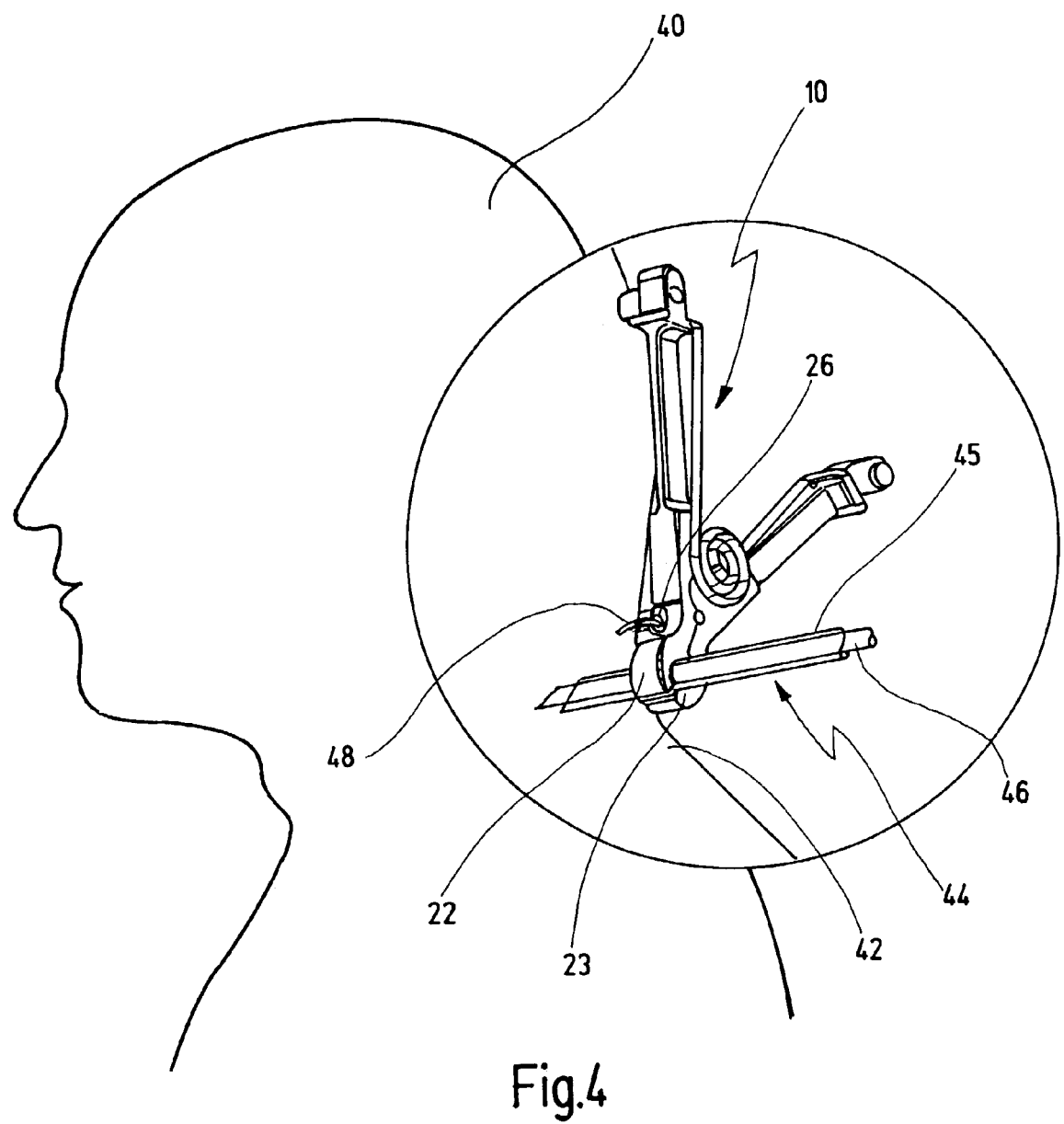
FIG. 4 shows a diagrammatic and partially enlarged view of a use of the device according to the invention from FIG. 1, in position on a patient's body.

At their distal end, the two forceps arms 12 and 13 each have a clamping jaw 22 and 23 which, in the closed end position, form an opening 24 in which a trocar sleeve 45 can be held, as is shown in FIG. 4.

In FIG. 1, the forceps 10 has, on the right and left sides of the forceps arms 12 and 13 and below the clamping jaws 22 and 23, two eye-like holes 26 and 27 via which the forceps 10 can be fixed to a body surface of a patient 40 by means of a surgical thread 48.

In FIG. 2, the forceps 10' is provided with a bracket 29 which is designed in the shape of a tab and has an eye-shaped hole 30. The bracket 29 is arranged so as to pivot about the hinge 14 on the forceps 10', as is indicated by the arrow 31. The forceps 10' can be fixed to the patient's body 40 by suturing through the eye-shaped hole 30 provided in the bracket 29.

Since the bracket 29 is arranged so as to pivot, it is also possible to press the forceps arms 12 and 13 together, and to place the thereby opened clamping jaws 22 and 23 around a trocar, when the forceps 10' as a whole is already fixed to the patient's body via the hole 30 in the bracket 29.

In a surgical intervention, the treating physician grips the two forceps arms 12 and 13 and presses them together counter to the force of the spring 16. In this way, the clamping jaws 23 and 24 open, by which means it is possible to place them around a trocar sleeve.

As is shown in FIG. 2, the forceps arms 12 and 13 can be designed with a thinner diameter for example in the section lying between the end bearing the pins 20 and 21 and the area of intersection. In this way, the forceps can be better gripped and the overall weight of the forceps can be further reduced.

By releasing the forceps arms 12 and 13, the clamping jaws 22 and 23 are pressed back into the closed position by the spring 16, as a result of which the clamping jaws 22 and 23 now securely enclose the trocar sleeve.

The size of the opening 24 formed by the two clamping jaws 22 and 23 depends on the trocar sleeve to be used and is, for example, 3 to 5 mm, with short forceps arms in particular for interventions in the neck area. The size of the opening 24 in other embodiments can be from 5 mm to 10 mm for example, and trocars with such an opening are used, for example, for all laparoscopy interventions.

The shape of the opening 24 formed by the clamping jaws 22 and 23 can vary and can be adapted to the circumference of the trocar sleeve which is to be held. Thus, the opening can, for example, be round or square, symmetrical or asymmetrical, etc. The surface of the clamping jaws 22 and 23 which faces the opening can additionally have longitudinal ridges and/or transverse ridges which provide for still better grip.

The trocar sleeve thus held in the forceps 10 or 10' cannot therefore be displaced in the axial direction, thereby avoiding a considerable risk of injury caused by the trocar sleeve penetrating farther into the patient.

The forceps 10 or 10' placed around a trocar sleeve can then be fixed by suturing them securely to the patient's body via the holes 26, 27 or 30. This avoids a situation where the inherent weight of the forceps causes it to slip from the surface of the patient's body. Giving the forceps a preferably light weight also reduces the load on the patient. A light weight is guaranteed by using a light metal, for example aluminum, or a plastic.

However, the forceps can also be secured to the patient's body by means of adhesive for example.

In the views in FIGS. 1 to 3, the holes 26, 27 and 30 are round, but they can also be square or oblong and can consist of sections with different diameters.

FIG. 3 shows another embodiment of the device according to the invention.

In this case, in the forceps 10", reference numbers 32 and 33 designate two further clamping jaws which, in the closed position, define a second opening 34. The clamping jaws 22, 23, 32 and 33 are arranged movably on the forceps arms 12 and 13 which are designed in the manner of rails in the distal area, as is indicated, for example, for clamping jaw 32 by arrow 36. The same applies to clamping jaws 23, 32 and 33.

Reference number 38 designates a locking screw which is guided laterally through the clamping jaw 22, and via which the clamping jaw 22 can be locked on the rail-like distal end of the forceps arm 12. Similar locking screws are located correspondingly on clamping jaws 23, 32 and 33. By means of this movable arrangement, the distance between the two openings 24 and 34 formed by the clamping jaws 22, 23 and 32, 33 can be adjusted. In this way it is possible, for example, for a first trocar to be held in the first opening 24 by the forceps 10" according to the invention and then, in proximity to the first trocar introduced, for a further trocar to be arranged in the patient's body. By means of the movable pair of clamping jaws 32, 33, this second trocar can be fixed in the opening 34 of the same forceps 10".

The possibility also exists of making only in each case the uppermost pair of clamping jaws movable, and also of arranging further clamping jaws on the forceps.

The device can be fixed to the patient's body by suturing via the hole 30 provided on the pivotable bracket 29.

FIG. 4 shows an example of a use of the device according to the invention. The device and an inserted trocar 44 are shown in an enlarged view.

Here, a surgical intervention is being performed in the neck area 42 of a patient 40. For this purpose, a trocar 44 with trocar sleeve 45 and trocar mandrel 46 is inserted in the neck area 42 of the patient 40. In order to fix the trocar sleeve 45 in the axial direction, the clamping jaws 22 and 23 of the forceps 10 are placed about the outside of the trocar sleeve 45.

In a next step, the forceps 10 is fixed to the patient 40 by suturing via the two openings 26 and 27. For this purpose, a thread, indicated by 48, is guided through the hole 26 of the forceps 10 into the neck area 42 of the patient 40, by which means the forceps 10 and thus also the trocar 44 are fixed securely in the neck area 42.

Because of the small size of the forceps 10, it is also possible to introduce further operating instruments in immediate proximity to the inserted and fixed trocar 44 and also to fix them with further forceps, without the treating physician being impeded by the forceps 10 already in place.

The invention claimed is:

1. A device for holding a trocar sleeve in its position of engagement in a body of a patient, wherein
   said device is designed as a forceps having two forceps arms intersecting one another and being connected to one another via a hinge at an area of intersection,
   said arms having distal ends, each of said ends being provided with at least one clamping jaw, a pair of clamping jaws defining in a closed position an opening where said opening is sized to be placed about an outside of a trocar sleeve,
   a spring having elongate ends being arranged between said forceps arms, which spring being supported on said forceps arms via its elongate ends, and forcing the clamping jaws into a closed position;
   and a bracket having a first end and a second end, where said first end includes a pivot located at said hinge for permitting said bracket to rotate about said hinge 360 degrees and where said second end extends away from said first end and includes a hole for permitting said device to be fixed on a patient.

2. The device of claim 1, wherein two holes are provided on sides of a distal end area of said forceps arms near a clamping jaw, via which holes said forceps can be fixed on a patient.

3. The device of claim 1, wherein said elongate ends of said spring are supported via two pins which are removable from said forceps arms.

4. The device of claim 3, wherein said pins are arranged in a proximal part of said forceps arms.

5. The device of claim 1, wherein said forceps arms having two pairs of clamping jaws, two clamping jaws of said two pairs defining in a closed position an opening in which portions of said two pairs of clamping jaws are situated at a distance from one another.

6. The device of claim 5, wherein said distance between said openings defined by said two pairs of clamping jaws is adjustable.

7. The device of claim 1, which is made of a material selected from the group consisting of metal, light metal and plastic.

8. The device of claim 7, wherein said metal is aluminum.

9. A device for holding a trocar sleeve in its position of engagement in a body of a patient, wherein
   said device is designed as a forceps having two forceps arms intersecting one another and being connected to one another via a hinge at an area of intersection,
   said arms having distal ends, each of said ends being provided with at least one clamping jaw, a pair of clamping jaws defining in a closed position an opening where said opening is sized to be placed about an outside of a trocar sleeve,
   a spring having elongate ends being arranged between said forceps arms, which spring being supported on said forceps arms via its elongate ends, and forcing the clamping jaws into a closed position,
   a bracket having a first end and a second end, where said first end includes a pivot located at said hinge for permitting said bracket to rotate about said hinge 360 degrees and where said second end extends away from said first end and includes a hole for permitting said device to be fixed on a patient;
   wherein at least one eye-like hole is provided at each of said two forceps arms, said at least one eye-like hole is provided in said area of intersection of each of said two forceps arms, so that said device can be fixed on a patient via said at least one eye-like hole.

10. The device of claim 9, wherein at least one hole is present in a pivotable bracket attached to said device.

11. The device of claim 9 wherein said elongate ends of said spring are supported via two pins which are removable from said forceps arms.

12. The device of claim 11, wherein said pins are arranged in a proximal part of said forceps arms.

13. The device of claim 9, wherein said forceps arms having two pairs of clamping jaws, two clamping jaws of said two pairs defining in a closed position an opening in which portions of said two pairs of clamping jaws are situated at a distance from one another.

14. The device of claim 13, wherein said distance between said openings defined by said two pairs of clamping jaws is adjustable.

15. The device of claim 9, which is made of a material selected from the group consisting of metal, light metal and plastic.

16. The device of claim 15, wherein said metal is aluminum.

17. A device for holding a trocar sleeve in its position of engagement in a body of a patient, comprising:
   a left forceps arm and a right forceps arm, each intersecting one another and being connected to one another at a hinge;
   a spring connected to and biasing said forceps arms to a closed position; and
   a bracket having a first end and a second end, where said first end is attached to said hinge for permitting said bracket to freely rotate about said hinge and where said second end extends away from said first end and includes an attachment mechanism for permitting said device to be fixed on a patient.

18. The device according to claim 17, wherein each of said forceps arms includes at least a part of an opening, and wherein in a closed position said forceps arms define an opening sized to be placed about an outside of a trocar sleeve.

19. The device according to claim 17, wherein said attachment mechanism is a hole.

* * * * *